(12) United States Patent
Hiskey et al.

(10) Patent No.: US 7,498,446 B2
(45) Date of Patent: Mar. 3, 2009

(54) PRIMARY EXPLOSIVES

(75) Inventors: Michael A. Hiskey, Los Alamos, NM (US); My Hang V. Huynh, Los Alamos, NM (US)

(73) Assignee: Los Alamos National Security, LLC, Los Alamos, NM (US)

( * ) Notice: Subject to any disclaimer, the term of this patent is extended or adjusted under 35 U.S.C. 154(b) by 431 days.

(21) Appl. No.: 11/055,248

(22) Filed: Feb. 10, 2005

(65) Prior Publication Data

US 2006/0030715 A1    Feb. 9, 2006

Related U.S. Application Data

(60) Provisional application No. 60/544,579, filed on Feb. 13, 2004.

(51) Int. Cl.
*C07D 257/04* (2006.01)

(52) U.S. Cl. .................................................. 548/250

(58) Field of Classification Search ................. 514/381; 548/250

See application file for complete search history.

(56) References Cited

OTHER PUBLICATIONS

Abstract—Charalambous, et al., Acta Crystallographica, Section C, 1987, C43(4), 659-61.*
Charalambous et. al, Acta Crystallographica, C43(4), 659-61.*

* cited by examiner

*Primary Examiner*—Rei-Tsang Shiao
*Assistant Examiner*—Susannah Chung
(74) *Attorney, Agent, or Firm*—Bruce H. Cottrell; Juliet A. Jones

(57) ABSTRACT

The present invention provides a compound of the formula $(Cat)^+_z[M^{++}(5\text{-nitro-}1H\text{-tetrazolato-}N2)^-_x(H_2O)_y]$ where x is 3 or 4, y is 2 or 3, x+y is 6, z is 1 or 2, and $M^{++}$ is selected from the group consisting of iron, cobalt, nickel, copper, zinc, chromium, and manganese, and $(Cat)^+$ is selected from the group consisting of ammonium, sodium, potassium, rubidium and cesium. A method of preparing the compound of that formula is also disclosed.

10 Claims, 1 Drawing Sheet

Cation = $NH_4^+$, $Na^+$, $K^+$, $Rb^+$, and $Cs^+$

PRIMARY EXPLOSIVES

RELATED APPLICATIONS

This application claims the benefit and priority of the filing of U.S. provisional application 60/544,579 filed Feb. 13, 2004.

STATEMENT REGARDING FEDERAL RIGHTS

This invention was made with government support under Contract No. W-7405-ENG-36 awarded by the U.S. Department of Energy. The government has certain rights in the invention.

FIELD OF THE INVENTION

The present invention relates generally to primary explosives and more particularly to lead-free primary explosives.

BACKGROUND OF THE INVENTION

Primary explosives are substances used in small quantities that when subjected to a flame, heat, impact, friction or an electric spark, generate a detonation wave. The detonation of the primary explosive initiates the secondary or main charge explosive or propellant. The main requirements for initiating explosives are sufficient sensitivity to be detonated reliably but not so sensitive as to be exceedingly dangerous to handle and sufficient thermal stability to not decompose on extended storage or thermal insult. Unfortunately, almost all currently used primaries contain lead in the form of either lead styphnate or lead azide. Devices using primary explosives are manufactured by the tens of million every year in the U.S. from primers for bullets to detonators for mining. Lead contamination at artillery ranges, both military and civilian, has become a major environmental issue.

Accordingly, the development of a lead-free primary explosive and a process of preparing a lead-free primary explosive have been sought.

SUMMARY OF THE INVENTION

In accordance with the purposes of the present invention, as embodied and broadly described herein, the present invention includes a compound of the formula $(Cat)^+_z[M^{++}(5\text{-nitro-1H-tetrazolato-N2})^-_x(H_2O)_y]$ where x is 3 or 4, y is 2 or 3, x+y is 6, z is 1 or 2, $M^{++}$ is selected from the group consisting of iron, cobalt, nickel, copper, zinc, chromium, and manganese, and $(Cat)^+$ is selected from the group consisting of ammonium, sodium, potassium, rubidium and cesium.

The present invention also includes a method of preparing metal complexes of the formula $(Cat)^+_z[M^{++}(5\text{-nitro-1H-tetrazolato-N2})^-_x(H_2O)_y]$ where x is 3 or 4, y is 2 or 3, x+y is 6, z is 1 or 2, and $M^{++}$ is selected from the group consisting of iron, cobalt, nickel, copper, zinc, chromium, and manganese, and $(Cat)^+$ is selected from the group consisting of ammonium, sodium, potassium, rubidium and cesium including admixing a metal salt and a salt of 5-nitrotetrazole in a suitable solvent, and, heating said admixture at temperatures and for time sufficient to form said metal complexes.

DETAILED DESCRIPTION

Figure 1:
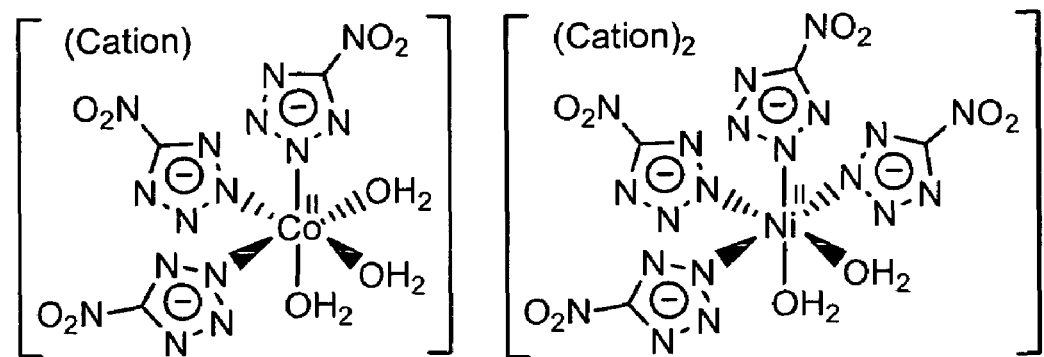
FIG. 1 shows structures of representative species of compounds of the present invention.
Figure 1:
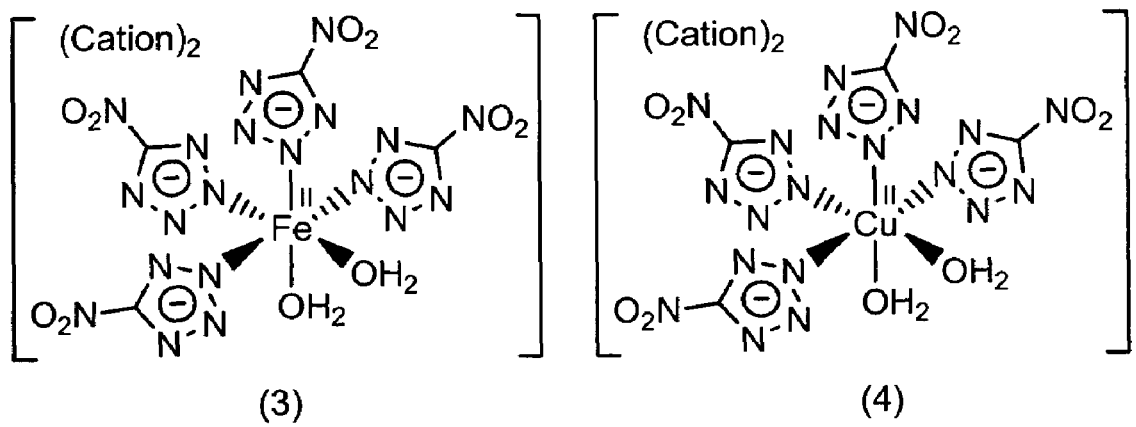

The present invention is concerned with primary explosives and in particular lead-free primary explosives. Among particular species of the lead-free primary explosives of the present invention are included the cobalt(II), nickel(II), iron (II) and copper(II) complexes shown in FIG. 1. Among particular species are included ammonium triaquatris(5-nitro-1H-tetrazolato-N2)cobaltate(II), ammonium diaquatetrakis (5-nitro-1H-tetrazolato-N2)nickelate(II), ammonium diaquatetrakis(5-nitro-1H-tetrazolato-N2)ferrate(II), ammonium diaquatetrakis(5-nitro-1H-tetrazolato-N2)cuprate(II), sodium triaquatris(5-nitro-1H-tetrazolato-N2)cobaltate(II), sodium diaquatetrakis(5-nitro-1H-tetrazolato-N2)nickelate (II), sodium diaquatetrakis(5-nitro-1H-tetrazolato-N2)ferrate(II), sodium diaquatetrakis(5-nitro-1H-tetrazolato-N2) cuprate(II). The complexes include a total of six ligands with two or three water ligands and three or four 5-nitrotetrazolate ligands depending upon the particular central metal atom. The compounds of the present invention offer the possibility of lead-free primary explosives.

The central metals of the compounds of the present invention are non-toxic. The metals can be selected from among cobalt, nickel, iron, copper, zinc, chromium, and manganese, preferably cobalt, nickel, iron and copper. An iron-based primary explosive has been sought for many years and may be most preferable.

The compounds of the present invention can be readily prepared by stirring the particular metal salt in water with the required amount of a salt of 5-nitrotetrazole, followed by refluxing for a suitable length of time, generally about one hour. The resultant complexes precipitate and can be simply filtered and washed with water giving greater than a 90 percent yield of analytically pure materials. The composition of the cation, $(Cat)^+$, is determined by which salt of 5-nitrotetrazole is utilized. The cation also has an affect on sensitivity and thermal stability with ammonium being the least sensitive and thermally stable while the alkali metal salts (sodium, potassium, rubidium and cesium) are more sensitive and thermally stable. All the compounds have thermal stability over 250° C. and densities >2.0 g/cm$^3$. In addition, these compounds have no sensitivity to water unlike metastable interstitial composite (MIC) based primary explosives. The water in the complexes is chemically bound and does not undergo any further reaction. In fact, the water may very well be required to "calm down" these materials allowing them to be worked with safely.

The 5-nitrotetrazolate complex of iron(III) was attempted with no success. It is believed that there is not enough electron density in iron(III) to support a complex ion with the electron deficient ligand of 5-nitrotetrazolate.

In the process of the present invention, metal complexes of the formula $(Cat)^+_z[M^{++}(5\text{-nitro-1H-tetrazolato-N2})^-_x(H_2O)_y]$ where x is 3 or 4, y is 2 or 3, x+y is 6, z is 1 or 2, and $M^{++}$ is selected from the group consisting of iron, cobalt, nickel, copper, zinc, chromium, and manganese, and $(Cat)^+$ is selected from the group consisting of ammonium, sodium, potassium, rubidium and cesium can be prepared by admixing a metal salt and a salt of 5-nitrotetrazole in a suitable solvent, and, heating the admixture at temperatures and for time sufficient to form the metal complexes. Suitable solvents for the reaction can include water and may include lower alcohols, with water being the preferred solvent. The admixture is generally heated at reflux so that with water it is at about 100° C. and the heating is maintained for about one hour although the time may be shorter or longer.

Each of the complexes prepared has been compared to the published literature values for lead azide and lead styphnate and the values are shown in Table 1. As can be seen in the Table, each ammonium metal complex has a higher detonation velocity than both lead azide and lead styphnate even though each has lower density. In addition each of the prepared materials is safer to work with than lead azide or lead styphnate in terms of sensitivity to impact, spark or friction initiation, but each is still sensitive enough to be classified as a primary explosive. The alkali metal salts such as sodium are have also been prepared, and they have comparable thermal stability when compared to the ammonium metal salts. Compared to the ammonium metal salts, the sodium metal salts have similar spark sensitivity but are more sensitive to impact and friction. Finally, each of the prepared materials, as an ammonium and sodium metal salt, has only slightly lower thermal stability when compared to lead azide or lead styphnate. However, they are much higher than the minimum temperature requirement of 200° C. Comparative values are given for PETN, which is pentaerythritol tetranitrate.

nium metal salts and 1 oz-3 in ball-drop test for the sodium metal salts. Friction sensitivities were determined with a BAM friction machine. Spark sensitivities were determined at 0.36 J. The sensitivity and performance values for lead azide and lead styphnate shown in Table 1 were taken from the published literature.

EXAMPLE 1

Preparation of ammonium triaquatris(5-nitro-1H-tetrazolato-N2)cobaltate(II) as follows. A solution of 0.501 g (1.72 mmol) hexaaquacobalt(II) perchlorate was dissolved in 30 ml of water and 0.682 g (5.17 mmol) of ammonium 5-nitrotetrazolate added with stirring. A pale yellow precipitate formed immediately. The suspension was brought to reflux for 2 hrs. The solution was cooled to room temperature. The solid was filtered, washed with water and methanol, and air-dried. Yield 0.74 g (91%). Analytically Calculated for $CoC_3H_{10}O_9N_{16}$: C, 7.62; H, 2.13; N, 47.37; O, 30.43. Found: C, 7.84; H, 1.82; N, 47.38; O, 29.62.

TABLE 1

| Complexes | $NH_4[Co^{II}(NT)_3(H_2O)_3]$ | $(NH_4)_2[Ni^{II}(NT)_4(H_2O)_2]$ | $(NH_4)_2[Fe^{II}(NT)_4(H_2O)_2]$ |
|---|---|---|---|
| d (g/cm$^3$) | 2.04 (Gas Pyc) | 2.44 (Gas Pyc) | 2.18 (Gas Pyc) |
| $V_D$ (km/sec) | 6.74 (@ 1.64 g/cm$^3$) | 7.02 (@ 1.73 g/cm$^3$) | 7.14 (@ 1.71 g/cm$^3$) |
| Spark (J) | >0.36 | >0.36 | >0.36 |
| Friction (kg) | 0.8 (vs 5.8 for PETN) | 1.5 (vs 5.8 for PETN) | 2.8 (vs 5.8 for PETN) |
| Impact (cm) | 22 (vs 14 for PETN) | 18 (vs 14 for PETN) | 25 (vs 14 for PETN) |
| DSC | 270° C. | 270° C. | 255° C. |

| Complexes | $NH_4[Cu^{II}(NT)_4(H_2O)_2]$ | $[Pb^{II}(N_3)_2]$ | $[Pb^{II}(styphnate)]\cdot H_2O$ |
|---|---|---|---|
| d (g/cm$^3$) | 1.94 (Gas Pyc) | 4.80 (X-ray) | 3.02 (X-ray) |
| $V_D$ (km/sec) | 7.39 (@ 1.71 g/cm$^3$) | 5.5 (@ 3.8 g/cm$^3$) | 5.2 (@ 2.9 g/cm$^3$) |
| Spark (J) | >0.36 | 0.0047 | 0.0002 |
| Friction (kg) | 0.6 (vs 5.8 for PETN) | 0.01 (vs 5.8 for PETN) | 0.04 (vs 5.8 for PETN) |
| Impact (cm) | 23 (vs 14 for PETN) | 9.6 (vs 14 for PETN) | 14.0 (vs 14 for PETN) |
| DSC | 265° C. | 315° C. | 282° C. |

| Complexes | $Na[Co^{II}(NT)_3(H_2O)_3]$ | $Na_2[Ni^{II}(NT)_4(H_2O)_2]$ | $Na_2[Fe^{II}(NT)_4(H_2O)_2]$ | $Na_2[Cu^{II}(NT)_4(H_2O)_2]$ |
|---|---|---|---|---|
| Spark (J) | >0.36 | >0.36 | >0.36 | >0.36 |
| Friction (kg) | <<0.5 | <<0.5 | <<0.5 | <<0.5 |
| Impact (1 oz-3 in ball-drop) | Positive | Positive | Positive | Positive |
| DSC | 264° C. | 265° C. | 250° C. | 259° C. |

The present invention is more particularly described in the following examples, which are intended as illustrative only since numerous modifications and variations will be apparent to those skilled in the art.

All compounds are sensitive primary explosives and should be worked with only behind appropriate shielding. All metal salts were obtained from commercial sources. Ammonium nitrotetrazolate was prepared by diazotization of 5-aminotetrazole in the presence of excess nitrite followed by extraction as the tri-laurylamine salt and displacement by ammonia. Upon addition of stoichiometric amount of ammonium hydroxide, sodium nitrotetrazolate forms quantitatively and is analytically pure. Elemental analysis was performed at Los Alamos National Laboratory. The data were in agreement to at least two elements within ±0.4%. Melting points were determined by differential scanning calorimetry (DSC) at 5° C./min. Densities were determined by helium gas pycnometry (Gas Pyc). Detonation velocities were determined on 0.25-inch (for cobalt, nickel and copper salts) and 0.5-inch (for iron salt) diameter pellets. Impact sensitivities were determined with a 2.5 kg weight (Type 12, cm) for the ammo-

EXAMPLE 2

Preparation of ammonium diaquatetrakis(5-nitro-1H-tetrazolato-N2)nickelate(II) was as follows. A solution of 0.502 g (1.73 mmol) hexaaquanickel(II) nitrate was dissolved in 30 ml of water and 0.912 g (6.90 mmol) of ammonium 5-nitrotetrazolate added with stirring. A lavender precipitate formed immediately. The suspension was brought to reflux for 2 hrs. The solution was cooled to room temperature. The solid was filtered, washed with water and methanol, and air-dried. Yield 0.94 g (93%). Analytically Calculated for $NiC_4H_{12}O_{10}N_{22}$: C, 8.19; H, 2.06; N, 52.50; O, 27.26. Found: C, 7.99; H, 1.81; N, 48.22; O, 25.23.

EXAMPLE 3

Preparation of ammonium diaquatetrakis(5-nitro-1H-tetrazolato-N2)ferrate(II) was as follows. A solution of 0.500 g (1.38 mmol) hexaaquairon(II) perchlorate was dissolved in 30 ml of water and 0.727 g (5.50 mmol) of ammonium 5-nitrotetrazolate added with stirring. An orange precipitate formed immediately. The suspension was brought to reflux for 2 hrs. The solution was cooled to room temperature. The solid was filtered, washed with water and methanol, and air-dried. Yield 0.77 g (96%). Analytically Calculated for $FeC_4H_{12}O_{10}N_{22}$: C, 8.22; H, 2.07; N, 52.75; O, 27.39. Found: C, 8.29; H, 1.79; N, 48.96; O, 27.62.

EXAMPLE 4

Preparation of ammonium diaquatetrakis(5-nitro-1H-tetrazolato-N2)cuprate(II) was as follows. A solution of 0.500 g (2.07 mmol) hexaaquacopper(II) nitrate was dissolved in 30 ml of water and 1.09 g (8.28 mmol) of ammonium 5-nitrotetrazolate added with stirring. A blue precipitate formed immediately. The suspension was brought to reflux for 2 hrs. The solution was cooled to room temperature. The solid was filtered, washed with water and methanol, and air-dried. Yield 1.14 g (93%). Analytically Calculated for $CuC_4H_{12}O_{10}N_{22}$: C, 8.12; H, 2.04; N, 52.07; O, 27.03. Found: C, 8.06; H, 1.80; N, 48.65; O, 27.73.

EXAMPLE 5

Preparation of sodium triaquatris(5-nitro-1H-tetrazolato-N2)cobaltate(II) was as follows. A solution of 0.500 g (1.72 mmol) hexaaquacobalt(II) perchlorate was dissolved in 30 ml of water and 0.892 g (5.15 mmol) of sodium 5-nitrotetrazolate added with stirring. A pale yellow precipitate formed immediately. The suspension was brought to reflux for 2 hrs. The solution was cooled to room temperature. The solid was filtered, washed with water and methanol, and air-dried. Yield 0.76 g (92%).

EXAMPLE 6

Preparation of sodium diaquatetrakis(5-nitro-1H-tetrazolato-N2)nickelate(II) was as follows. A solution of 0.500 g (1.72 mmol) hexaaquanickel(II) nitrate was dissolved in 30 ml of water and 1.19 g (6.90 mmol) of sodium 5-nitrotetrazolate added with stirring. A lavender precipitate formed immediately. The suspension was brought to reflux for 2 hrs. The solution was cooled to room temperature. The solid was filtered, washed with water and methanol, and air-dried. Yield 0.92 g (90%).

EXAMPLE 7

Preparation of sodium diaquatetrakis(5-nitro-1H-tetrazolato-N2)ferrate(II) was as follows. A solution of 0.500 g (1.38 mmol) hexaaquairon(II) perchlorate was dissolved in 30 ml of water and 0.954 g (5.51 mmol) of sodium 5-nitrotetrazolate added with stirring. An orange precipitate formed immediately. The suspension was brought to reflux for 2 hrs. The solution was cooled to room temperature. The solid was filtered, washed with water and methanol, and air-dried. Yield 0.77 g (94%).

EXAMPLE 8

Preparation of sodium diaquatetrakis(5-nitro-1H-tetrazolato-N2)cuprate(II) was as follows. A solution of 0.500 g (2.07 mmol) hexaaquacopper(II) nitrate was dissolved in 30 ml of water and 1.43 g (8.28 mmol) of sodium 5-nitrotetrazolate added with stirring. A blue precipitate formed immediately. The suspension was brought to reflux for 2 hrs. The solution was cooled to room temperature. The solid was filtered, washed with water and methanol, and air-dried. Yield 1.18 g (95%).

Although the present invention has been described with reference to specific details, it is not intended that such details should be regarded as limitations upon the scope of the invention, except as and to the extent that they are included in the accompanying claims.

What is claimed is:

1. A method of preparing metal complexes of the formula $(Cat)^+_z[M^{++}(5\text{-nitro-1H-tetrazolato-N2})^-_x(H_2O)_y]$ where x is 3 or 4, y is 2 or 3, x+y is 6, z is 1 or 2, and $M^{++}$ is selected from the group consisting of iron, cobalt, nickel, copper, zinc, chromium, and manganese, and $(Cat)^+$ is selected from the group consisting of ammonium, sodium, potassium, rubidium and cesium comprising:

admixing a metal hexaaqua salt and a salt of 5-nitrotetrazole selected from among ammonium, sodium, potassium, rubidium and cesium salts of 5-nitrotetrazole in a suitable solvent; and, heating said admixture at temperatures and for time sufficient to form said metal complexes of the formula $(Cat)^+_z[M^{++}(5\text{-nitro-1H-tetrazolato-N2})^-_x(H_2O)_y]$ where x is 3 or 4, y is 2 or 3, x+y is 6, z is 1 or 2, and $M^{++}$ is selected from the group consisting of iron, cobalt, nickel, copper, zinc, chromium, and manganese, and $(Cat)^+$ is selected from the group consisting of ammonium, sodium, potassium, rubidium and cesium.

2. The method of claim 1, wherein said suitable solvent is water and said heating is at reflux for at least about 1 hour.

3. The method of claim 1, wherein the metal complex is ammonium triaquatris(5-nitro-1H-tetrazolato-N2)cobaltate(II).

4. The method of claim 1, wherein the metal complex is ammonium diaquatetrakis(5-nitro-1H-tetrazolato-N2)nickelate(II).

5. The method of claim 1, wherein the metal complex is ammonium diaquatetrakis(5-nitro-1H-tetrazolato-N2)ferrate(II).

6. The method of claim 1, wherein the metal complex is ammonium diaquatetrakis(5-nitro-1H-tetrazolato-N2)cuprate(II).

7. The method of claim 1, wherein the metal complex is sodium triaquatris(5-nitro-1H-tetrazolato-N2)cobaltate(II).

8. The method of claim 1, wherein the metal complex is sodium diaquatetrakis(5-nitro-1H-tetrazolato-N2)nickelate(II).

9. The method of claim 1, wherein the metal complex is sodium diaquatetrakis(5-nitro-1H-tetrazolato-N2)ferrate(II).

10. The method of claim 1, wherein the metal complex is sodium diaquatetrakis(5-nitro-1H-tetrazolato-N2)cuprate(II).

* * * * *